US011166451B2

(12) United States Patent
Ilyin et al.

(10) Patent No.: US 11,166,451 B2
(45) Date of Patent: Nov. 9, 2021

(54) METHOD FOR LIVING TISSUE PRESERVATION

(71) Applicant: Rich Technologies Holding Company, LLC, Buffalo, NY (US)

(72) Inventors: Ilya Ilyin, Wayland, MA (US); Semyon Kogan, Newton, MA (US); William E. Grieshober, Jr., East Amherst, NY (US); James S. Jones, St. Simons Island, GA (US); Alexander N. Shumeev, St. Petersburg (RU); Stanislav A. Kolchanov, St. Petersburg (RU); Yana A. Filkina, St. Petersburg (RU); Yuriy Punin, St. Petersburg (RU); Natella I. Enukashvily, St. Petersburg (RU)

(73) Assignee: Rich Technologies Holding Company, LLC, Buffalo, NY (US)

( * ) Notice: Subject to any disclaimer, the term of this patent is extended or adjusted under 35 U.S.C. 154(b) by 304 days.

(21) Appl. No.: 14/345,740

(22) PCT Filed: Sep. 26, 2012

(86) PCT No.: PCT/US2012/057211
§ 371 (c)(1),
(2) Date: Mar. 19, 2014

(87) PCT Pub. No.: WO2013/049118
PCT Pub. Date: Apr. 4, 2013

(65) Prior Publication Data
US 2014/0227678 A1    Aug. 14, 2014

Related U.S. Application Data

(60) Provisional application No. 61/539,009, filed on Sep. 26, 2011.

(51) Int. Cl.
*A01N 1/02*   (2006.01)
*C12N 5/078*  (2010.01)
*A61J 1/14*   (2006.01)
*A61M 1/02*   (2006.01)

(52) U.S. Cl.
CPC .......... *A01N 1/021* (2013.01); *A01N 1/0263* (2013.01); *A01N 1/0284* (2013.01); *A01N 1/0289* (2013.01); *C12N 5/0644* (2013.01); *A61J 1/1468* (2015.05); *A61M 1/0272* (2013.01); *A61M 2202/0427* (2013.01); *C12N 2500/02* (2013.01)

(58) Field of Classification Search
CPC .... A01N 1/0221; A01N 1/021; A01N 1/0263; A01N 1/0284
See application file for complete search history.

(56) References Cited

U.S. PATENT DOCUMENTS

| | | |
|---|---|---|
| 3,228,838 A | 1/1966 | Rinfret |
| 3,344,617 A | 10/1967 | Rinfret |
| 4,473,552 A | 9/1984 | Jost |
| 4,943,287 A | 7/1990 | Carmen |
| 4,946,326 A | 8/1990 | Schvester |
| 5,108,656 A | 4/1992 | Schvester |
| 5,237,959 A | 8/1993 | Bergeron |
| 5,309,868 A | 5/1994 | Tomiyama |
| 5,555,845 A | 9/1996 | Flynn |
| 5,597,599 A | 1/1997 | Smith |
| 5,622,867 A | 4/1997 | Livesey |
| 5,789,151 A | 8/1998 | Bitensky et al. |
| 6,068,148 A | 5/2000 | Weiler |
| 6,238,716 B1 | 5/2001 | Prins |
| 6,342,261 B1 | 1/2002 | Spencer |
| 8,158,339 B2 | 4/2012 | I.Iyin et al. |
| 10,098,340 B2 | 10/2018 | Grieshober, Jr. et al. |
| 10,123,528 B2 | 11/2018 | I.Iyin et al. |
| 2003/0158507 A1 | 8/2003 | Serebrennikov |
| 2005/0002873 A1 | 1/2005 | Harmon |
| 2005/0136125 A1 | 6/2005 | Roth |
| 2005/0147692 A1 | 7/2005 | Roth |
| 2005/0170019 A1 | 8/2005 | Roth |
| 2007/0078113 A1 | 4/2007 | Roth |
| 2007/0110821 A1 | 5/2007 | Petzelt et al. |
| 2008/0031971 A1 | 2/2008 | Petzelt |
| 2008/0171726 A1 | 2/2008 | Petzelt |
| 2008/0085329 A1 | 4/2008 | Roth |
| 2008/0131514 A1 | 6/2008 | Truong-Le |
| 2008/0171093 A1 | 7/2008 | Roth |
| 2008/0171725 A1 | 7/2008 | Roth |
| 2009/0011051 A1 | 1/2009 | Roth |
| 2009/0081785 A1 | 3/2009 | Ho et al. |
| 2009/0286220 A1* | 11/2009 | Sheleg ................. A01N 1/0221 435/1.3 |
| 2009/0311340 A1 | 12/2009 | Franks et al. |
| 2010/0009334 A1 | 1/2010 | Ilyin et al. |
| 2010/0196996 A1 | 8/2010 | Kilic et al. |
| 2012/0196362 A1 | 8/2012 | I.Iyin et al. |
| 2012/0225416 A1 | 9/2012 | Yoshida et al. |

FOREIGN PATENT DOCUMENTS

| | | |
|---|---|---|
| CN | 1195965 A | 10/1998 |
| WO | 1993019629 | 3/1993 |

(Continued)

OTHER PUBLICATIONS

Freeman "How waterworks", How stuff works 2007, p. 1-8.*

(Continued)

*Primary Examiner* — Blaine Lankford
(74) *Attorney, Agent, or Firm* — Michael Best & Friedrich LLP

(57) ABSTRACT

A method for platelet preservation comprising placing a composition comprising platelets in a gas mixture comprising xenon and oxygen under pressure of about 0-10 Bars at a first temperature of about 18° C.-37° C. for a first period of time, and then subsequently cooling the composition to a second temperature of about 0,1° C.-6° C., and holding the composition under the pressure and in the second temperature for a second period of time.

37 Claims, No Drawings

(56) References Cited

FOREIGN PATENT DOCUMENTS

| WO | 2005039600 | | 10/2004 |
|---|---|---|---|
| WO | 2005041655 | | 2/2005 |
| WO | 2005039291 | | 5/2005 |
| WO | 2005041656 | | 5/2005 |
| WO | 2006113914 | | 10/2006 |
| WO | 2008040002 | | 4/2008 |
| WO | 2010005959 | A1 | 1/2010 |
| WO | 2010088364 | A2 | 8/2010 |

OTHER PUBLICATIONS

Yuan "Platelet Products" pdf dated Feb. 23, 2011 and downloaded from http://pathology.ucla.edu/workfiles/2-3-platelet-products.pdf.*

U.S. Search Authority, International Search Report dated Nov. 30, 2012, for corresponding PCT application No. PCT/US2012/057211.

De Rossi et al., "Xenon does not affect human platelet function in vitro" Anesth. Analg. 93:635-640 (2001).

Sheleg et al., "Cardiac mitrochondrial membrane stability after deep hypothermia using xenon clathrate cryostatis Protocol" J. Clin. Exp. Pathol., 1:440-447 (2008).

Lozano, "Platelets come back in from the cold", Blood 111:2951 (2008).

Petzelt et al., "Prevention of neurotoxicity in hypoxic cortical neurons by the noble gas xenon"; Life Sciences 72:1909-1918 (2003).

Wandall et al., "Galactysylation does not prevent the rapid clearance of long-term 40C-stored platelets", Blood 111:3249-3256 (2008).

Josefsson et al., "Platelet Storage Temperature—How Low Can It Go?", Transfu. Med. Hemother. 34:253-261 (2007).

Sanders et al., "Xenon_ elemental anesthesia in clinical practice" British Medical Bulletin 71:115-135 (2005).

Poppert et al., "The cryoprotective properties of various gases in kidney preservation" Zschr. Urol. 66:481-488 (1973) [English translation of German article].

Philp et al., "Effects of elevated pressures of inert gases on cytolsolic free Ca2+ of human platelets stimulated with ADP" Cell Calcium 14:525-529 (1993).

Shcherbakov et al., "Gas influenced immortality" Chemistry and Life 8:34-39 (2006) [English translation of Russian article].

Khlusov et al., "Cell Effect of Zenon In Vitro under Hypothermal Conditions" Cell Technologies in Biology and Medicine 2:510-513(2007).

Office Action issued from the Chinese Patent Office for related Application No. 2019109344106 dated Mar. 25, 2021 (17 Pages including English Translation).

Boswell et al., "Platelet-Rich Plasma: A Milieu of Bioactive Factors", 2012, Arthroscopy: The Journal of Arthroscopic and Related Surgery, vol. 28, No. 3 pp. 429-439.

Cookson et al., "Platelet apoptosis and activation in platelet concentrates stored for up to 12 days in plasma or additive solution", Transfusion Medicine, 2010, vol. 20 pp. 392-402.

De Boer et al., "Early Apoptosis Largely Accounts for Functional Impairment of CD34 + Cells in Frozen-Thawed Stem Cell Grafts", Journal of Hematotherapy & Stem Cells Research, 2002, vol. 11, pp. 951-963.

Karas et al., "T Cell Receptor-induced Activation and Apoptosis in Cycling Human T Cells Occur throughout the Cell Cycle", Molecular Biology of the Cell, 1999, vol. 10, pp. 4441-4450.

Pimentel-Munoa et al., "Regulated Commitment of TNF Receptor Signaling: A Molecular Switch for Death or Activation", Immunity, 1999, vol. 11, pp. 783-798.

Shapiro et al., "Future Trends 1n Islet Cell Transplantation", Diabetes Technologies & Therapeutics, 2000, vol. 2 No. 3, pp. 449-452.

Spaggiari et al., Antiapoptotic activity of argon and xenon, Cell Cycle, 2013, vol. 12, pp. 2636-2642.

Valavaniz et al., "Model Cell Lines for the Study of Apoptosis in Vitro", Method in Cell Biology, 2001, vol. 66, pp. 417-436.

International Search Report with Written Opinion for related Application No. PCT/US2012/023790, dated Apr. 5, 2010 (6 Pages).

Dumont et al., "Exploratory in vitro study of red blood cell storage containers formulated with alternative plasticizer", Transfusion, Jul. 2012, vol. 52, pp. 1439-1445.

International Search Report with Written Opinion for related Application No. PCT/US2013/070677, dated Mar. 20, 2014 (13 Pages).

Second Examination Report issued from the Canada Patent Office for related Application No. 2892006 dated Aug. 14, 2020 (4 Pages).

Examination Report issued from the India Patent Office for related Application No. 4560/DELNP/2015 dated Nov. 26, 2020 (3 Pages with English Translation).

* cited by examiner

METHOD FOR LIVING TISSUE PRESERVATION

The present invention claims priority on U.S. Provisional Patent Application Ser. No. 61/539,009 filed Sep. 26, 2011, which is incorporated herein by reference.

The present invention relates generally to the field of living tissue preservation, more particularly relates to preservation of platelets, and even more particularly relates to preservation of platelets in a xenon and oxygen atmosphere.

BACKGROUND OF THE INVENTION

The current standard method for platelet storage comprises keeping platelets in a bag with constant shaking. This method is limited to five days of storage time and requires keeping the platelets at room temperature because platelets do not tolerate refrigeration. Thus, there is an ongoing need for methods for increasing platelet storage time. The present invention meets these and other needs.

SUMMARY OF THE INVENTION

The present invention provides a method for platelet preservation that can be used to extend the life of useable platelets beyond five (5) days. The method generally comprises obtaining a composition comprising platelets and exposing it to a gas mixture, and keeping the composition at a refrigerated temperature. The composition comprising platelets is generally kept under pressure; however, this is not required.

All ranges disclosed herein, including, but not necessarily limited to, percentages of gases, temperatures, and units of pressure, include each range end point and all integers there between and numbers to the tenth and hundredth decimal point.

In one non-limiting aspect of the present invention, the gas mixture includes xenon and oxygen. The gas mixture can include trace amounts of other gasses. Generally at least about 95% of the gas mixture includes xenon and oxygen, typically the gas mixture include at least about 98% xenon and oxygen, still more particularly, the gas mixture include at least about 99% xenon and oxygen, yet still more particularly the gas mixture include at least about 99.5% xenon and oxygen, and yet still even more particularly the gas mixture include at least about 99.9% xenon and oxygen. The gas mixture includes more xenon than oxygen. In one non-limiting embodiment of the invention, the gas mixture includes about 79%-95% xenon. In another non-limiting embodiment of the invention, the gas mixture includes about 80%-92% xenon. In still another non-limiting embodiment of the invention, the gas mixture includes about 82%-91% xenon. In yet another non-limiting embodiment of the invention, the gas mixture includes about 85%-90% xenon. In still yet another non-limiting embodiment of the invention, the gas mixture includes about 86%-88% xenon. In another non-limiting embodiment of the invention, the gas mixture includes about 5%-21% oxygen. In still another non-limiting embodiment of the invention, the gas mixture includes greater that 5% oxygen and less than 21% oxygen. In yet another non-limiting embodiment of the invention, the gas mixture includes about 6%-18% oxygen. In still yet another non-limiting embodiment of the invention, the gas mixture includes about 10%-16% oxygen. In another non-limiting embodiment of the invention, the gas mixture includes about 12%-14% oxygen.

In another and/or alternative non-limiting aspect of the present invention, the method includes the step of the composition comprising platelets being exposed to the gas mixture under a certain pressure. In one non-limiting embodiment of the invention, the composition comprising platelets is exposed to the gas mixture under a gas pressure of about 0-10 Bars. In another non-limiting embodiment of the invention, the composition comprising platelets is exposed to the gas mixture under a gas pressure of about 1-8 Bars. In still another non-limiting embodiment of the invention, the composition comprising platelets is exposed to the gas mixture under a gas pressure of about 2-6 Bars. In yet another non-limiting embodiment of the invention, the composition comprising platelets is exposed to the gas mixture under a gas pressure of about 3-5 Bars. In still yet another non-limiting embodiment of the invention, the composition comprising platelets is exposed to the gas mixture under a gas pressure of about 3.5-5 Bars.

In still another and/or alternative non-limiting aspect of the present invention, the method includes the step of maintaining the composition that includes the platelets for a first period of time at a first temperature in the presence of the gas mixture. In one non-limiting embodiment of the invention, the composition comprising the platelets is held for a first period of time at a first temperature in the presence of the gas mixture, which first temperature is about 18° C.-37° C. In one non-limiting embodiment, the composition comprising the platelets is held for a first period of time at a first temperature in the presence of the gas mixture, which first temperature is about 18° C.-23° C. In still one non-limiting embodiment, the composition comprising the platelets is held for a first period of time at a first temperature in the presence of the gas mixture, which first temperature is about 20° C.-22° C. The first period of time is selected to enable the xenon in the gas mixture to become partially for fully saturated in the composition comprising platelets. In one non-limiting embodiment of the invention, the first period of time allows the xenon in the gas mixture to reach at least about 60% of full saturation in the composition comprising platelets. In another non-limiting embodiment of the invention, the first period of time allows the xenon in the gas mixture to reach at least about 75% of full saturation in the composition comprising platelets. In still another non-limiting embodiment of the invention, the first period of time allows the xenon in the gas mixture to reach at least about 90% of full saturation in the composition comprising platelets. In yet another non-limiting embodiment of the invention, the first period of time allows the xenon in the gas mixture to reach about 95%-100% of full saturation in the composition comprising platelets. Generally during the first period of time, about 2-20% of the xenon in the gas mixture dissolves into the composition comprising platelets, and typically during the first period of time, about 5-18% of the xenon in the gas mixture dissolves into the composition comprising platelets, and more typically during the first period of time, about 8-15% of the xenon in the gas mixture dissolves into the composition comprising platelets. In another non-limiting embodiment of the invention, the first period of time is about 5 seconds to 10 hours. In still another non-limiting embodiment of the invention, the first period of time is about 60 seconds to 5 hours. In yet another non-limiting embodiment of the invention, the first period of time is about 60 seconds to 4 hours. In yet another non-limiting embodiment of the invention, the first period of time is about 60 seconds to 3.5 hours. In still yet another non-limiting embodiment of the invention, the first period of time is about 3-3.5 hours. As can be appreciated, the temperature and/or pressure can be constant or be varied while the composition comprising platelets is being partially or fully saturated by the xenon in the gas mixture.

In still another and/or alternative non-limiting aspect of the present invention, the method includes the step of cooling the composition comprising platelets to a second temperature after the composition comprising platelets has been partially or fully saturated by the xenon in the gas mixture. Generally, the composition comprising platelets is cooled to a second temperature that is above the freezing point of the composition comprising platelets for a second period of time. In one non-limiting embodiment of the invention, the composition comprising platelets is cooled to a second temperature of about 0.1° C.-6° C. for a second period of time. In another non-limiting embodiment of the invention, the composition comprising platelets is cooled to a second temperature of about 3° C.-6° C. for a second period of time. The second period of time is generally at least 5 days and up to about a month. In one non-limiting embodiment, the second period of time is greater than 5 days and up to about 21 days. In another non-limiting embodiment, the second period of time is greater than 5 days and up to about 14 days.

In yet another and/or alternative non-limiting aspect of the present invention, the method includes the step of placing the composition comprising platelets in a container that enables a majority of the platelets in the container to lay flat or substantially flat while the composition comprising platelets is 1) partially or fully saturated with xenon, 2) subsequently cooled to the second temperature after partial or full saturation with the xenon gas, and/or 3) stored or the second period of time at the second temperature. In one non-limiting embodiment, the container is designed to cause majority of the platelets in the container to lay flat or substantially flat while the composition comprising platelets is cooled to the second temperature after partial or full saturation with the xenon gas. In still another non-limiting embodiment, the container is designed to cause majority of the platelets in the container to lay flat or substantially flat while the composition comprising platelets is partially or fully saturated with xenon.

In one non-limiting specific embodiment of the invention, there is provided a method for platelet preservation comprising placing a composition comprising platelets in a gas mixture comprising or consisting of 79%-95% xenon and 5%-21% oxygen under pressure from 3.5-5 bars at a temperature from 18° C.-23° C. for a period of time, and then cooling the composition to a cooled temperature from 3° C.-6° C., and holding the composition under the pressure and in the cooled temperature for a period of time. The composition under the pressure and in the cooled temperature can be stored in a refrigerator of a period of from 5 days to 14 days. The cooling chamber can be used for cooling the composition and subsequently the cooling chamber is used for storage of the composition. The composition can be placed into a container permeable to a gas mixture and the composition can be exposed to the gas mixture in a hermetically sealed chamber. The container can comprise a hermetically sealed vessel equipped with a cover permeable for the gas mixture. A bag made of material permeable to the gas mixture can be used as the container. At least 200 ml of the composition comprising the platelets can be placed into the bag, and subsequently the composition can be kept in the gas mixture and under pressure for at least 3 hours. The composition can be kept in the gas mixture and under pressure without additional pumping of gas mixture into the hermetically sealed chamber, and the cooling of the composition can be started from the time point of stabilization of the gas mixture pressure in the hermetically sealed chamber, and with the stabilization resulting from saturation of platelet plasma with the gas mixture. Prior to transfusing the composition comprising the platelets, the composition can be kept under pressure not exceeding 1 atmosphere and at a temperature of 18° C.-23° C. for at least a time period sufficient for ambient heating of the composition to the said temperature.

The present invention is suitable for preserving platelets, such as platelets present in plasma. Conventional bag or specially configured containers designed for storing blood products can be used in the method. The bag or container can be designed and the material can be selected so that the bag or container is impermeable or permeable to xenon and oxygen. The method can be performed using commercially available equipment that is capable of supplying a gas mixture to the bag or container, such as, but not limited to, a hermetically sealed chamber. The hermetically sealed chamber can be designed to withstand an internal gas pressure of at least 5-10 bars; however, this is not required. Cooling of composition comprising platelets can be performed using existing refrigeration equipment (e.g., conventional refrigerators, etc.), in which preserved blood products can be cooled and stored; however, this is not required.

Without intending to be constrained by any particular theory, it is considered that the method facilitates diffusion of xenon and oxygen into the composition comprising the platelets (including diffusion into the platelets themselves), and that this takes place while the platelets are kept in a gas mixture with xenon content from 79% to 95% and oxygen content from 5% to 21% at a first temperature of about 18° C.-37° C. and at a pressure of 0-10 Bars. It is considered that partial or full saturation of the platelets with xenon facilitates subsequent storage the platelets at a temperature from 0.1° C.-6° C., with preservation of viability and functionality of the platelets.

The method can be used with any composition comprising platelets, which include, but are not necessarily limited to, compositions comprising or consisting of blood plasma, platelet rich plasma, or isolated platelets. The platelets can be obtained using conventional techniques from any animal, such as any mammal, which includes human beings.

In contrast to previously published methods, the present invention does not require the addition of starches to the composition comprising the platelets. Moreover, the data related to the present invention demonstrates that a certain amount of oxygen in the gas mixture to which the platelets are exposed is desirable to preserve platelet viability. In particular, since certain metabolic processes are still taking place in the platelets while at refrigerated temperatures, oxygen is needed for aerobic respiration. The requirement of platelets for oxygen is most pronounced when preserving large volumes of platelet plasma, such as volumes above 200 ml, and in such cases, having from 5%-21% oxygen present in the xenon/oxygen gas mixture is desirable. In various embodiments, the volume of the composition comprising the platelets in the bag or container was from about 5 ml-400 ml or more. In certain embodiments, the composition comprising the platelets is stirred and/or gently shaken to increase contact with the oxygen in the composition; however, this is not required. Generally, the composition comprising the platelets is not shaken or stirred when being cooled at the second temperature; however, this is not required.

In still another non-limiting aspect of the present invention, to perform the method of the present invention, the platelet composition is placed into a gas-permeable bag or container, and the gas-permeable bag or container is placed into a hermetically sealed chamber in which the gas mixture is added. In particular, a hermetically sealed vessel equipped with a cover permeable for the gas mixture or bag or container made of material permeable to gas mixtures (e.g. bags conventionally used for the storage of platelet plasma) could be used as such bags or containers.

In various embodiments, the first time period during which the composition comprising platelets is kept in the gas mixture under a pressure of 0-10 Bars can be determined based on determining a cessation of an increase in pressure of the gas mixture in a hermetically sealed chamber, without additional pumping of the gas mixture into the chamber. For example, xenon and oxygen can be added to the container to achieve a pressure of between 0-10 Bars. In one non-limiting embodiment, the pressure is about 3-4 Bars. The addition of the gas mixture can be stopped, and if desired, the chamber can be detached from the gas mixture source and held, with for example shaking. During shaking, the pressure will decrease and stabilize. For example, if the composition comprising platelets is about 4 bars of total pressure, the pressure in the bag or container will reduce and stabilizes at levels of about 3.5-3.9 bars, which is believed to be indicative that the xenon gas has adequately penetrated the platelets. After this drop in pressure, the container is cooled to the second temperature according to the method of the invention. Due to solubility of the gas mixture being higher at lower temperatures, the pressure inside the bag or container may drop further during cooling. As one non-limiting example, a pressure inside the container of about 3.8 bars at ambient temperature may drop to about 3.6 bars during cooling to the second temperature.

In one non-limiting embodiment, when using a bag or container made of material permeable to a gas mixture and which contains 200-400 ml of a platelet composition, a first time period of about 2-5 hours of exposure to the gas mixture under a pressure of about 0-10 Bars at the first temperature can be used; however, this is not required.

Cooling the platelet composition down the second temperature can be started in various embodiments before, concurrent with, or after the time point where gas mixture pressure stabilization in the hermetically sealed chamber occurs.

Prior to using the preserved platelets for transfusion, the pressure in the bag or container can be released so that the platelets are at atmospheric pressure, and the temperature can be raised by, for example, removing the composition from refrigeration at the second temperature and allowing it rise to a temperature of about 18° C. to 37° C. In particular, the hermetically sealed chamber can be taken out of the cooling chamber at the second temperature, after which the hermetic sealing is unsealed, and the container with the platelet composition is removed from the container and kept at room temperature and atmospheric pressure for a period sufficient for ambient heating of the composition to room temperature, and for equilibration of the pressure and/or release of the gas mixture to the surrounding environment. To reduce the time of the release of the gas mixture, the bag or container could be placed under the conditions of decreased pressure (as compared to atmospheric pressure), i.e., a vacuum; however, this is not required.

The present invention is compared to certain attributes of previously published methods as described in the Example below.

EXAMPLE 1

The following equipment and materials were used in conducted experiments.

The platelet plasma (obtained from donated blood via apheresis) was placed into plastic bags produced by Baxter (Baxter's plastic bags PL 1813/1).

A hermetically sealed chamber, into which bags with platelet plasma were placed for storage, was used in the experiments. This chamber was designed to withstand internal pressure of at least 5 bars and specially manufactured in such a way that it was equipped with ducts intended for supplying xenon and oxygen under pressure and with flow meters and manometers intended for controlling the amount and proportion of gases supplied into the chamber and gas pressure inside the chamber. Xenon and oxygen were supplied from individual high-pressure bottles.

A medical-purpose refrigerator with a pre-set temperature of 4° C. was used as the cooling chamber.

Evaluation of platelet plasma suitability after preservation and storage was conducted in terms of the following parameters.

Number of Cells

A parameter indicating the degree of population preservation after storage. This parameter is calculated as a percentage from the number of cells at the beginning of experiment—prior to beginning the platelet plasma preservation.

PH Level

One of the parameters determining the viability and functionality of platelets (ideal value of pH is 7.4). With pH values below 6.2 or higher than 7.8, platelets (transfused to patients) will be quickly removed from the blood flow by systems for decontaminating human body. The level of pH within the range 6.2-7.8 is considered to be a good outcome of preservation. The best outcome in terms of pH value is pH equal to 7.4.

Lactate Level

A parameter indicating the viability of cells during storage under the conditions of oxygen deficit. Lactate level increases during storage because of metabolic processes. Higher concentrations of lactate become toxic for platelets. Furthermore, when lactate concentration is higher than 20 mM/l, the value of plasma pH can reduce down to 6.2 and lower. The viability and functionality of platelets are degraded as a consequence of this pH drop. An acceptable level of lactate in the stored platelet plasma should not exceed the value of lactate level for platelet plasma that has been stored at room temperature for a period of up to 5 days.

Glucose Level

A parameter that is also related to metabolism and reflects a "food reserve for cells." If the glucose level in the platelet plasma decreases significantly after storage, a certain percentage of platelets may be non-viable and after transfusion, and such platelets would be unable to perform their function and would be eliminated from the blood.

Results of platelet storage obtained by performing one non-limiting embodiment of the present invention were evaluated based on the above-indicated parameters. Three control samples of human platelet preparations were also evaluated in terms of these parameters for the purpose of comparison, as follows:

Sample 1 (Fresh)

60 ms fresh human platelet plasma concentrate obtained by aphaeresis.

Sample 2 (Control RT)

Platelet plasma after storage for a period of 5 days at room temperature (standard storage method).

Sample 3 (Control +4)

Platelet plasma after storage for a period of 14 days in a refrigerator at a temperature of 4° C. and under atmospheric pressure.

The following results of experiments were obtained.

| Sample number | Conditions | Storage time, days | Cell number | pH | Lactate, mM | Glucose, mM |
|---|---|---|---|---|---|---|
| 1 | Fresh | 0 | 100% | 7.7 | 0.6 | 18.4 |
| 2 | Control RT | 5 | 93% | 7.2 | 10.6 | 11.8 |
| 3 | Control +4 | 14 | 41% | 7.3 | 10.4 | 12.5 |
| 4 | $O_2$-0% | 14 | 49% | 8.1 | 11.6 | 12.5 |
| 5 | $O_2$-5% | 14 | 46% | 8.1 | 9.6 | 12.3 |
| 6 | $O_2$-13% | 14 | 93% | 7.4 | 8.0 | 16.2 |
| 7 | $O_2$-21% | 14 | 45% | 7.4 | 7.7 | 12.1 |

Samples 4-7 in the Table were preserved and stored in the indicated gas percentages using from 0 to 21% oxygen, and where the remaining percentage of the gas mixture was xenon.

Results of experiments show:

1) In terms of the number of platelet cells, the best result was obtained for a oxygen concentration of about 13% (Sample 6).

2) In terms of pH level, the best results were obtained for oxygen concentrations of 13% and 21% (Samples 6 and 7).

3) In terms of lactate level, the best result was obtained for an oxygen concentration of 21% (Sample 7). However, the result obtained for an oxygen concentration of 13% was only slightly different, and results for other samples were different by 25-50% as compared to the best result (Sample 7).

4) In terms of glucose level, acceptable results were obtained for all samples, in which oxygen was present in the composition of the gas mixture. The best result was obtained for oxygen concentration of 13% (Sample 6).

Results of experiments illustrate that the method of the present invention provides for longer term storage of preserved platelet plasma as compared to previously described methods. Furthermore, the longer-storage term is achieved for significantly larger volumes of platelet plasma than has been previously described, which allows using the present invention with bags that are conventionally employed for platelet plasma storage.

The experiments demonstrated suitable results using a lowest oxygen concentration of 5%, and that oxygen in concentrations higher than 21% are toxic for the platelet cells.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween. The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

We claim:

1. A method for platelet preservation that can be used to extend the life of useable platelets beyond five days comprising the steps of:
    a) placing a composition comprising platelets in a gas mixture comprising more than 50% xenon and 5-21% oxygen, wherein a combined content of xenon and oxygen in said gas mixture is at least 95%;
    b) maintaining said composition comprising platelets in the presence of said gas mixture for a first period of time and at a first temperature until said xenon in said gas mixture has saturated said composition comprising platelets to at least 60% saturation, said first temperature is above a freezing point of said composition;
    c) cooling said composition comprising platelets that is at least partially saturated with xenon to a second temperature, said second temperature being less than said first temperature, said second temperature above a freezing point of said composition, said second temperature being about 0.1° C.-6° C., said pressure at said second temperature is no more than 5 bars; and,
    d) holding said composition comprising platelets at said second temperature for a second period of time, said first period of time is less than said second period of time, a pH of said composition at said second temperature is no lower than 6.2.

2. The method as defined in claim 1, wherein said gas mixture includes 79%-95% xenon and 5%-21% oxygen.

3. The method as defined in claim 1, wherein said gas mixture includes 86%-88% xenon and 12%-14% oxygen.

4. The method as defined in claim 2, wherein said gas mixture includes 86%-88% xenon and 12%-14% oxygen.

5. The method as defined in claim 1, wherein said first temperature is 18° C.-37° C.

6. The method as defined in claim 4, wherein said first temperature is 18° C.-37° C.

7. The method as defined in claim 1, wherein said first temperature is 18° C.-23° C.

8. The method as defined in claim 6, wherein said first temperature is 18° C.-23° C.

9. The method as defined in claim 1, wherein step of maintaining said composition comprising platelets in said presence of said gas mixture for a first period of time and at a first temperature including subjecting said composition comprising platelets to a pressure of at least 1.1 Bar.

10. The method as defined in claim 8, wherein step of maintaining said composition comprising platelets in said presence of said gas mixture for a first period of time and at a first temperature including subjecting said composition comprising platelets to a pressure of at least 1.1 Bar.

11. The method as defined in claim 1, wherein step of maintaining said composition comprising platelets in said presence of said gas mixture for a first period of time and at a first temperature including subjecting said composition comprising platelets to a pressure of 1.1-5 Bars.

12. The method as defined in claim 10, wherein step of maintaining said composition comprising platelets in said presence of said gas mixture for a first period of time and at a first temperature including subjecting said composition comprising platelets to a pressure of 1.1-5 Bars.

13. The method as defined in claim 1, wherein said first period of time is about 5 seconds to ten hours.

14. The method as defined in claim 12, wherein said first period of time is about 5 seconds to ten hours.

15. The method as defined in claim 1, wherein said first period of time is about 60 seconds to five hours.

16. The method as defined in claim 14, wherein said first period of time is about 60 seconds to five hours.

17. The method as defined in claim 1, wherein said second temperature is about 3° C.-6° C.

18. The method as defined in claim 16, wherein said second temperature is about 3° C.-6° C.

19. The method as defined in claim 1, wherein said second period of time is 5-21 days.

20. The method as defined in claim 18, wherein said second period of time is 5-21 days.

21. The method as defined in claim 1, said composition comprising platelets is at least 80% of full saturation with said xenon gas during said first period of time and at said first temperature.

22. The method as defined in claim 20, said composition comprising platelets is at least 80% of full saturation with said xenon gas during said first period of time and at said first temperature.

23. The method as defined in claim 1, wherein said composition is placed into a bag or container permeable to said gas mixture and said composition is exposed to said gas mixture in a hermetically sealed chamber.

24. The method as defined in claim 22, wherein said composition is placed into a bag or container permeable to said gas mixture and said composition is exposed to said gas mixture in a hermetically sealed chamber.

25. A method for platelet preservation that can be used to extend the life of useable platelets beyond five days comprising the steps of:
   a) placing a composition comprising platelets in a gas mixture comprising more than 50% xenon and 5-21% oxygen, wherein a combined content of xenon and oxygen in said gas mixture is at least 95%;
   b) maintaining said composition comprising platelets in the presence of said gas mixture for a first period of time and at a pressure and a first temperature until said xenon in said gas mixture has saturated said composition comprising platelets to at least 75% saturation, said first temperature is 18° C.-37° C., said pressure is at least 0.1 bar and up to 5 bar, said first period of time is about 5 seconds to 10 hours, said first temperature is above a freezing point of said composition;
   c) cooling said composition comprising platelets that is at least partially saturated with xenon to a second temperature, said second temperature being less than said first temperature, said second temperature above a freezing point of said composition, said second temperature being about 0.1° C.-6° C., said pressure at said second temperature is no more than 5 bars; and,
   d) holding said composition comprising platelets at said second temperature for a second period of time, said first period of time is less than said second period of time, a pH of said composition at said second temperature is about 6.2-7.8.

26. The method as defined in claim 25, wherein said combined content of xenon and oxygen in said gas mixture is at least 99%, said gas mixture includes at least 82 vol. % xenon and at least 6 vol. % oxygen.

27. The method as defined in claim 25, wherein said combined content of xenon and oxygen in said gas mixture is at least 99.5%, said gas mixture includes at least 85 vol. % xenon and at least 10 vol. % oxygen.

28. The method as defined in claim 25, wherein said combined content of xenon and oxygen in said gas mixture is at least 99.9%, said gas mixture includes at least 86 vol. % xenon and at least 12 vol. % oxygen.

29. The method as defined in claim 25, wherein said pressure in step b) is 3.5-5 bars, said first period of time is 60 seconds to 4 hours, said first temperature is 18° C.-23° C., said platelets are maintained in the presence of said gas mixture for said first period of time and at said first temperature and pressure until said xenon in said gas mixture has saturated said composition comprising platelets to at least 90% saturation, said second period of time is at least 5 days, and further including the step of placing said platelets in a gas-permeable container while said platelets are at least partially saturated with said gas mixture and maintained at said second temperature for said second period of time.

30. The method as defined in claim 26, wherein said pressure in step b) is 3.5-5 bars, said first period of time is 60 seconds to 4 hours, said first temperature is 18° C.-23° C., said platelets are maintained in the presence of said gas mixture for said first period of time and at said first temperature and pressure until said xenon in said gas mixture has saturated said composition comprising platelets to at least 90% saturation, said second period of time is at least 5 days, and further including the step of placing said platelets in a gas-permeable container while said platelets are at least partially saturated with said gas mixture and maintained at said second temperature for said second period of time.

31. The method as defined in claim 27, wherein said pressure in step b) is 3.5-5 bars, said first period of time is 60 seconds to 4 hours, said first temperature is 18° C.-23° C., said platelets are maintained in the presence of said gas mixture for said first period of time and at said first temperature and pressure until said xenon in said gas mixture has saturated said composition comprising platelets to at least 90% saturation, said second period of time is at least 5 days, and further including the step of placing said platelets in a gas-permeable container while said platelets are at least partially saturated with said gas mixture and maintained at said second temperature for said second period of time.

32. The method as defined in claim 28, wherein said in step b) pressure is 3.5-5 bars, said first period of time is 60 seconds to 4 hours, said first temperature is 18° C.-23° C., said platelets are maintained in the presence of said gas mixture for said first period of time and at said first temperature and pressure until said xenon in said gas mixture has saturated said composition comprising platelets to at least 90% saturation, said second period of time is at least 5 days, and further including the step of placing said platelets in a gas-permeable container while said platelets are at least partially saturated with said gas mixture and maintained at said second temperature for said second period of time.

33. The method as defined in claim 25, wherein said pressure in step b) is 3.5-4 bars.

34. The method as defined in claim 29, wherein said pressure in step b) is 3.5-4 bars.

35. The method as defined in claim 30, wherein said pressure in step b) is 3.5-4 bars.

36. The method as defined in claim 31, wherein said pressure in step b) is 3.5-4 bars.

37. The method as defined in claim 32, wherein said pressure in step b) is 3.5-4 bars.

\* \* \* \* \*